United States Patent
Hardwick et al.

(10) Patent No.: US 9,544,729 B2
(45) Date of Patent: Jan. 10, 2017

(54) APPARATUS AND METHOD FOR GEOLOCATION INTELLIGENCE

(71) Applicant: GE Intelligent Platforms, Inc., Charlottesville, VA (US)

(72) Inventors: Peter Hardwick, Foxboro, MA (US); Daniel Carvalho, Foxboro, MA (US); Blayne Watt, Foxboro, MA (US)

(73) Assignee: GE INTELLIGENT PLATFORMS, INC., Charlottesville, VA (US)

( * ) Notice: Subject to any disclaimer, the term of this patent is extended or adjusted under 35 U.S.C. 154(b) by 0 days.

(21) Appl. No.: 14/440,113

(22) PCT Filed: Feb. 25, 2013

(86) PCT No.: PCT/US2013/027568
§ 371 (c)(1),
(2) Date: May 1, 2015

(87) PCT Pub. No.: WO2014/070220
PCT Pub. Date: May 8, 2014

(65) Prior Publication Data
US 2015/0365794 A1      Dec. 17, 2015

Related U.S. Application Data

(60) Provisional application No. 61/721,623, filed on Nov. 2, 2012.

(51) Int. Cl.
*H04W 24/00*     (2009.01)
*H04W 4/02*      (2009.01)
(Continued)

(52) U.S. Cl.
CPC .......... *H04W 4/021* (2013.01); *A61K 31/4439* (2013.01); *A61K 31/498* (2013.01);
(Continued)

(58) Field of Classification Search
CPC ............................ H04W 4/008; H04W 4/206
(Continued)

(56) References Cited

U.S. PATENT DOCUMENTS 6,122,520 A    9/2000 Want et al.
6,631,310 B1   10/2003 Leslie
(Continued)

FOREIGN PATENT DOCUMENTS

EP    1477911 A1    11/2004
EP    2078928 A1    7/2009
(Continued)

OTHER PUBLICATIONS

International Search Report and Written Opinion issued in connection with corresponding application PCT/US2013/027568 dated Aug. 5, 2014.
(Continued)

*Primary Examiner* — Kiet Doan
(74) *Attorney, Agent, or Firm* — GE Global Patent Operation; Scott R. Stanley

(57) ABSTRACT

Location information relating to a changeable location of a mobile device is received. An automatic determination is made as to whether an asset is closest in geographic proximity to the location of the mobile device where the asset is selected from a plurality of assets. Based upon the selected asset, mobile interface information is automatically retrieved where this information is specifically associated with the selected asset. The mobile interface information is automatically sent to the mobile device for display to the user without any interaction from the user.

6 Claims, 8 Drawing Sheets

(51) Int. Cl.

| | | |
|---|---|---|
| *A61K 45/06* | (2006.01) | |
| *A61K 31/4439* | (2006.01) | |
| *A61K 31/498* | (2006.01) | |
| *A61K 31/519* | (2006.01) | |
| *A61K 31/5377* | (2006.01) | |
| *A61K 31/554* | (2006.01) | |

(52) U.S. Cl.
CPC ........ *A61K 31/519* (2013.01); *A61K 31/5377* (2013.01); *A61K 31/554* (2013.01); *A61K 45/06* (2013.01); *H04W 4/026* (2013.01)

(58) Field of Classification Search
USPC ............... 455/457, 456.2, 456.1, 433, 456.3; 707/724, 759, 600; 345/633; 701/438, 701/517; 700/226
See application file for complete search history.

(56) References Cited

U.S. PATENT DOCUMENTS

| | | | |
|---|---|---|---|
| 6,714,778 | B2 | 3/2004 | Nykaenen et al. |
| 7,007,228 | B1 | 2/2006 | Carro |
| 7,010,294 | B1 | 3/2006 | Pyotsia et al. |
| 7,266,429 | B2 | 9/2007 | Travaly et al. |
| 7,444,188 | B2 | 10/2008 | De Meyer et al. |
| 7,483,944 | B2 | 1/2009 | Parupudi et al. |
| 7,490,153 | B1 | 2/2009 | Krishnan et al. |
| 7,620,621 | B2 | 11/2009 | Fuselier et al. |
| 7,730,482 | B2 | 6/2010 | Illowsky et al. |
| 7,769,767 | B2 | 8/2010 | Petersen |
| 7,860,994 | B2 | 12/2010 | Rensin et al. |
| 7,890,483 | B1 | 2/2011 | Aaron et al. |
| 8,234,294 | B2 | 7/2012 | Shlaes et al. |
| 8,255,411 | B1 | 8/2012 | Carpenter et al. |
| 8,296,655 | B2 | 10/2012 | Lusty |
| 8,589,069 | B1 * | 11/2013 | Lehman ................. G01C 21/20 340/995.1 |
| 2002/0017155 | A1 | 2/2002 | Aota |
| 2002/0073165 | A1 | 6/2002 | McNulty et al. |
| 2002/0138196 | A1 | 9/2002 | Polidi et al. |
| 2006/0086781 | A1 | 4/2006 | Jung et al. |
| 2006/0184508 | A1 | 8/2006 | Fuselier et al. |
| 2006/0270421 | A1 | 11/2006 | Phillips et al. |
| 2007/0078535 | A1 | 4/2007 | Bromley et al. |
| 2008/0194240 | A1 | 8/2008 | Dowling et al. |
| 2009/0089288 | A1 | 4/2009 | Petersen |
| 2010/0188088 | A1 | 7/2010 | Nielsen et al. |
| 2010/0325127 | A1 | 12/2010 | Chaudhuri et al. |
| 2011/0099142 | A1 | 4/2011 | Karjalainen et al. |
| 2011/0296346 | A1 | 12/2011 | Chen et al. |
| 2011/0313657 | A1 | 12/2011 | Myllymaki et al. |
| 2012/0019674 | A1 | 1/2012 | Ohnishi et al. |
| 2012/0036140 | A1 | 2/2012 | Nielsen et al. |
| 2012/0131044 | A1 | 5/2012 | Nusser et al. |
| 2012/0136865 | A1 | 5/2012 | Blom et al. |
| 2012/0173981 | A1 | 7/2012 | Day |
| 2012/0233158 | A1 | 9/2012 | Braginsky et al. |
| 2012/0242648 | A1 | 9/2012 | Baier et al. |
| 2012/0245944 | A1 | 9/2012 | Gruber et al. |
| 2012/0260161 | A1 | 10/2012 | Ishigami |
| 2012/0269116 | A1 | 10/2012 | Xing et al. |
| 2013/0040665 | A1 * | 2/2013 | Lee ....................... H04W 4/028 455/457 |

FOREIGN PATENT DOCUMENTS

| | | |
|---|---|---|
| EP | 2136274 A1 | 12/2009 |
| EP | 2509334 A1 | 10/2012 |
| WO | 0129642 B1 | 4/2001 |
| WO | 2003102738 A2 | 12/2003 |
| WO | 2008008724 A2 | 1/2008 |

OTHER PUBLICATIONS

Peter Hardwick et al., Apr. 23, 2015, U.S. Appl. No. 14/437,993.
Peter Hardwick, May 1, 2015, U.S. Appl. No. 14/440,108.
Peter Hardwick, Apr. 29, 2015, U.S. Appl. No. 14/439,370.
Kjeldskov, ""Just-in-Place" Information for Mobile Device Interfaces", Mobile HCI '02 Proceedings of the 4th International Symposium on Mobile Human-Computer Interaction, vol. No. 2411, pp. 271-275, Sep. 18, 2002.
Perich et al., "Collaborative Joins in a Pervasive Computing Environment", Technical Report TR-CS-03-28, Jul. 28, 2003.
Yau et al., "A Context-Sensitive Middleware for Dynamic Integration of Mobile Devices with Network Infrastructures", Journal of Parallel and Distributed Computing, vol. No. 64, Issue No. 2, pp. 301-317, Feb. 2004.
Robinson et al., "A Context-Sensitive Service Discovery Protocol for Mobile Computing Environments", International conference on Mobile Business, pp. 565-572, Jul. 11-13, 2005.
Zipf et al., "Implementing Adaptive Mobile GI Services Based on Ontologies: Examples From Pedestrian Navigation Support", Computers, Environment and Urban Systems, vol. No. 30, Issue No. 6, pp. 784-798, Nov. 2006.
Mountain et al., "Geographic Information Retrieval in a Mobile Environment: Evaluating the Needs of Mobile Individuals", Journal of Information Science, vol. No. 33, Issue No. 5, pp. 515-530, Oct. 2007.
Xu et al., "Context-Aware Content Filtering & Presentation for Pervasive & Mobile Information Systems", Proceedings of the 1st international conference on Ambient media and systems, pp. 1-8, Feb. 11, 2008.
Pattath et al., "Contextual Interaction for Geospatial Visual Analytics on Mobile Devices", Proceedings of SPIE-IS&T Electronic Imaging, SPIE, vol. No. 7256, pp. 72560H-1-72560H-12, Jan. 28, 2009.
Raubal et al., "A Formal Model for Mobile Map Adaptation", Location Based Services and TeleCartography II, Section I, pp. 11-34, 2009.
Thain, "The Power of Context Sensitive Alerts in Mobile Applications", Jul. 2, 2012.
Anonymous, "MobiTrans—A Mobile Web Solution Framework", IP.com, Jul. 5, 2012.
PCT Search Report and Written Opinion issued in connection with related Application No. PCT/US2013/027571 on Jun. 5, 2013.
PCT Search Report and Written Opinion issued in connection with related Application No. PCT/US2013/027569 on Jul. 23, 2013.
PCT Search Report and Written Opinion issued in connection with corresponding Application No. PCT/US2013/027568 on Aug. 5, 2014.

* cited by examiner

APPARATUS AND METHOD FOR GEOLOCATION INTELLIGENCE

CROSS REFERENCES TO RELATED APPLICATIONS

This application claims benefit under 35 U.S.C. §119 (e) to U.S. Provisional Application No. 61/721,623 entitled "Geolocation Intelligence via Automatic Navigation and Field of View Filtering" filed Nov. 2, 2012, the content of which is incorporated herein by reference in its entirety.

Utility application entitled "Apparatus and method of Content Containment" naming as inventors Robert Molden and Peter Hardwick, U.S. application Ser. No. 14/439,370;

Utility application entitled "Apparatus and Method for Intelligent Querying and Filtering" naming as inventor Peter Hardwick, U.S. application Ser. No. 14/440,108; and Utility application entitled "Apparatus and Method for Dynamic Actions based upon Context" naming as inventors Robert Molden and Peter Hardwick, U.S. application Ser. No. 14/437,993, all of which are being filed on the same day as the present application and the contents of all of which are incorporated herein by reference in their entireties.

BACKGROUND OF THE INVENTION

Field of the Invention

The subject matter disclosed herein relates to the utilization of geolocation information to provide geo-spatial intelligence for automatic navigation systems.

Brief Description of the Related Art

Participants in the mobile application and server markets still hold the belief that simply ordering data with some type of relationships and allowing a user to browse through those relationships to access important data is sufficient. However, this is no longer the case, as users are expected to either know a large amount about their relational information or undergo an unacceptably large number of manual operations to obtain desired results.

In the case of the relational knowledge requirements, users are expected to traverse some large relationship representations in an attempt to obtain desired data. Such a process is tedious and error prone. For example, on a mobile device, requiring a large amount of user input is oftentimes difficult and impossible to perform in specific situations.

In another scenario, users are often provided with empty search boxes made up of various search capabilities requiring them to manually input various types of information. In this case, users must know what type of information they desire, must correctly enter in this information into the required search field, and must sort through a potential large list of results if their searches caused a large number of results. On a mobile device, for example, causing a large number of results could result in significant delays based on network bandwidth and may potentially result in hardware resource issues due to inefficient hardware constraints. Additionally, requiring users to manually type in information (e.g., into edit boxes) is a less than ideal solution for physical devices that only posses a digital means of input such as a screen keyboard or similar input mechanism.

While both of the above-mentioned previous approaches address the similar issue of allowing a user access to their requested data, neither approach provides an efficient and automatic, or intelligent solution.

BRIEF DESCRIPTION OF THE INVENTION

Approaches for automatic navigation and Field of View filtering are provided. As used herein "automatic navigation" means that data is selectively presented to a user (e.g., at a mobile user with some sort of visualization such as a web page). In one example, information concerning the nearest asset to the user is presented. In other aspects, a geofence may be used and associated with particular assets and information concerning an asset may be provided to a user automatically upon entering the geofence. In still other aspects, a Field of View (FoV) may be associated with a client application (e.g., a mobile client). In this case, only assets within the FoV have their information displayed. Users can also selectively choose and filter out specific data. In some aspects, the convenience of the present approaches enables users to be provided specified data without significant user interaction. The approaches described herein also allow users access to this information with minimal delay.

Using the approaches described herein, large amounts of data can be filtered with ease. Another advantage is that users can filter data such that it is not transferred across a limited network, thus maintaining network resources.

In many of these embodiments, location information relating to a changeable location of a mobile device is received. An automatic determination is made as to whether an asset is closest in geographic proximity to the location of the mobile device where the asset is selected from a plurality of assets. Based upon the selected asset, mobile interface information is automatically retrieved and this information is specifically associated with the selected asset. The mobile interface information is automatically sent to the mobile device for display to the user without any interaction from the user.

In other aspects, the mobile interface information is received at the mobile device and presented to the user on a display of the mobile device. In other aspects, one or more of the plurality assets has defined about it a geofence and the geofence defines a boundary about the asset. In yet other aspects, a detection of the mobile device is made when the user enters the periphery of the geofence. After detection, information concerning the appropriate asset can be displayed.

In some other aspects, a current Field of View is defined for a client application. The Field of View defines a geographic area and the client application is being operated on a mobile device. Assets that are disposed within the current Field of View are determined. First information concerning the assets that are geographically located within the Field of View is displayed and second information concerning assets that are not geographically located within the Field of View is not displayed. The first information is displayed as a mobile interface display.

In some aspects, the assets are associated with control devices. In some examples the Field of View is generally circular in shape while in other examples the Field of View is generally non-circular in shape.

In others of these embodiments, an apparatus for providing graphical information to a user includes an interface and a controller. The interface has an input and an output and the input is configured to receive location information relating to a changeable location of a mobile device. The controller is coupled to the interface and is configured to automatically determine an asset that is closest in geographic proximity to the location of the mobile device, the asset being selected from a plurality of assets. The controller is further configured to, based upon the selected asset, automatically retrieve mobile interface information that is specifically associated with the selected asset. The controller is further configured to automatically send the mobile interface information to the mobile device for display to the user via the output of the interface without any interaction from the user.

BRIEF DESCRIPTION OF THE DRAWINGS

For a more complete understanding of the disclosure, reference should be made to the following detailed description and accompanying drawings wherein.

Figure 1:
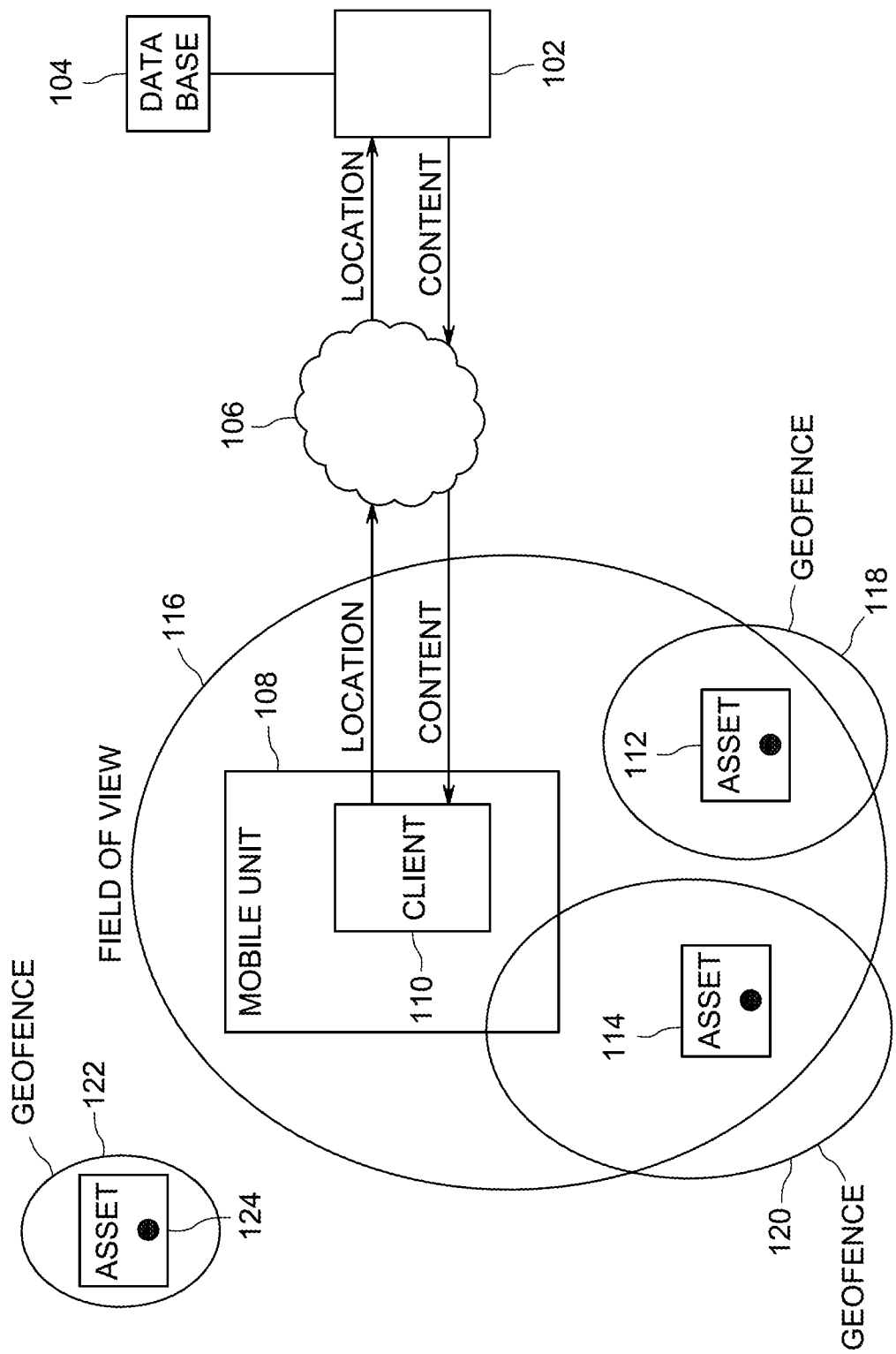
FIG. 1 comprises a block diagram of a system that provides automatic navigation and Field of View features according to various aspects of the present invention.

Skilled artisans will appreciate that elements in the figures are illustrated for simplicity and clarity. It will further be appreciated that certain actions and/or steps may be described or depicted in a particular order of occurrence while those skilled in the art will understand that such specificity with respect to sequence is not actually required. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION OF THE INVENTION

In the approaches described herein, the utilization of geolocation information is facilitated. For example, the various types of visualizations (e.g., mobile interface information such as web pages or the like) presented to a user can be altered based upon an asset that is closest to the user. This aspect provides an automatic navigation feature in which visualizations related to a single asset are automatically presented to users (e.g., users at mobile devices) without the manual intervention of these users. For instance, information concerning the nearest asset or nearest two assets may be presented. In still other aspects, information can be displayed regarding assets that are within the Field of View of a user. Separately or together, these approaches provide an automatic filtering procedure in which often the most relevant information is displayed. In these approaches, the geospatial information of a mobile device user and/or asset is utilized as a type of context and leveraged to filter data that is presented to a user.

When the automatic navigation and Field of View aspects are combined, an increased level of geospatial intelligence for an application is provided. Together these two aspects are referred to as "geo-intelligence." Geospatial intelligence may include one of these elements, both, or none at all. Further, Field of View is a filter and does not require auto navigation in order to function.

In some examples, the automatic navigation aspect is based upon the location of a user and the location of another item of interest. A system having a series of items of interest, or assets, which have been tagged in some manner with (or otherwise possesses) geospatial location identifying information can provide information to a user who is geospatially located within some proximity of one or more items of interest. In one example of these approaches, the nearest asset in the Field of View of a mobile client is presented to a user.

The automatic navigation information can be utilized with any object or device that has geospatial information associated with it. The auto navigation approaches presented herein provide for automatic information retrieval for data related to assets and automatic presentation of this information to a user. More specifically, auto navigation displays information or provides a new display/visualization of information based on the proximity to a given asset (e.g., or proximity to other assets). In some examples, the approaches described herein also automatically switch to provide information about other, different asset when the user moves to closer proximity of that other asset. Each asset can be specified to have a different proximity such that a user may have to be closer to one asset in order to be considered as being within its proximity. The proximity of an asset can be considered to be a description of a radius which can be used to describe a circle or any other shape or combinations of shapes. The circle (or shape) can be considered the geo fence of that asset.

In another aspect, the filtering of collections of assets is provided. For any given type of visualization or location within an application, lists, groups, or other collections of information can be filtered to include only the information belonging to assets within a certain distance from a user. That distance from a user describes a radius and that radius can be used to describe a circle. Any asset within the circle can be said to be within a users Field of View (FoV). Any asset within the FoV will be displayed, and those assets that fall outside of the FoV will not be displayed. Although a circle with a radius is described herein as an example shape of a Field of View, it will be appreciated that any type of shape whether regular or irregular may be used. A FoV could also be defined as the collections of multiple areas whether they be intersecting, overlapping or separate.

The approaches described herein overcome various problems prevalent in computing, but have become more burdensome with the proliferation of mobile devices and the expansion of a mobile workforce. First, the approaches described herein provide a simple mechanism to quickly and easily bring the most desirable data to a user at any given time, with little or no actual interaction required. A user knows where they are and what asset they are near. The present approaches contrast with previous systems that either make users browse through a series of hard coded visualizations trying to find the one that applies to the asset they are interested. The present approaches facilitate the presentation of the data to the user with very little or no interaction and enable filtering solutions such that data is not transferred across a limited network and resources are not utilized on limited hardware unless that data is necessary and prevalent.

The present approaches also allow for automatic switching of context of an application to identify one or more assets a user is within proximity of. As previously mentioned, the present approaches are not limited to geospatial information being used to determine assets of interest. However, in the examples described herein geospatial information is used exclusively to form a primary list of assets. Thus, in contrast to previous approaches, the desired information, displays, visualizations, and data presented to the user with as little user interaction and delay as possible (often no interaction).

Field of View (FoV) advantageously overcomes many of the disadvantages associated with large amounts of data. FoV provides a type of geospatial filtering such that any functionality that operates on assets does not have to retrieve or manipulate an entire set of assets at any time. FoV provides filtering in a geospatial sense such that only those assets within a FoV of the user are considered for operations. Operations may include calculations, notifications, display in lists for selection, and so forth.

Still another advantage of the approaches described herein is the ability to remove from a user's consideration large amounts of data. For large systems, the need to efficiently retrieve and operate on only the relevant data is important for allowing a system to scale while maintaining performance. The present approaches allow organization of data such that only the data of interest, that meeting the criteria, such as geospatial proximity, will be considered. This includes reducing the amount of data communicated between servers and other devices. This becomes particularly important in mobile applications where network bandwidth is restrictive and hardware is less powerful.

Referring now to FIG. 1, one example of an approach for presenting graphical information to a user is described. The system includes a server 102, a database 104, a network 106, and a mobile unit 108. The mobile unit 108 includes a client 110. A first asset 112 and a second asset 114 are disposed in proximity to the mobile unit 108 and within a Field of View 116. The first asset 112 has an associated first geofence 118 and the second asset has an associated second geofence 120. A third asset 124 has an associated third geofence 122. However, the third asset is not in the Field of View (FoV) 116 of the client 110. The position associated with a particular asset is shown as a point in the drawing.

The server 102 is any processing device that executes programmed software. In this sense, the server 102 may be any combination of hardware and programmed software. In one example, the server 102 receives location information and determines the closest asset. For example, the server 102 compares known latitude, longitude, and elevation components to determine the distances between objects (e.g., the distance between the mobile unit 108 and an asset). In other examples, the server 102 determines the two closest assets. In some other examples, other criteria besides geographic nearness may be used, for instance, assets that are deemed the most important. In yet other examples, multiple criteria may be used. In still other examples, the server 102 uses the Field of View 116 to determine all assets within this Field of View 116. Again, other criteria may also be used to filter the assets that are within the Field of View 116 for presentation to the user.

The database 104 is any type of memory storage device and may include any combination of data storage devices such as ROMs, RAMs, and so forth. Other examples of memories are possible. The network 106 is any type of communications network such as the Internet, a cellular phone network, or any combinations of these or other types of networks. Other examples of networks are possible.

The mobile unit 108 is any mobile device such as a personal computer, cellular phone, pager, or personal digital assistant. Other examples of mobile devices are possible. Location information of the mobile device is determined by any known approach such as using a satellite system to determine the location or using known approaches used in cellular telephone systems. The location information resides at the mobile unit 108, for example, in an appropriate data structure.

The client 110 is any type of programmed software application or combination of applications. In other examples, the client may be any combination or hardware or software.

The first asset 112, the second asset 114, and the third asset 124 are any type of electronic device, or combinations of devices. In other examples, they may be any type of object whatsoever, provided the object has accessible location information associated with it. In one example, they may be automation controllers or simply controllers. These controllers or control devices control or manage the execution of various functions. For example, robotic controllers (e.g., those that utilize microprocessors) control the functions of a robot and the robot can perform various manufacturing tasks. Assembly line controllers are used to control the various functions performed on or at an assembly line. Consumer device controllers are used to control the operation and functioning of any type of consumer device (e.g., security system, lighting system, heating system, traffic light or pump control). Other examples of controllers and the functions provided are possible.

The first geofence 118, the second geofence 120, and the third geofence 122 define a boundary of an asset. The geofences 118, 120 and 122 may be represented as a data structure (e.g., an array of information) including the latitude, the longitude, and the altitude of the asset. Other examples of data structures may be used to represent the geofences. The server 102 may determine when a particular mobile device or client enters the boundary of a geofence. It will be appreciated that a mobile device or client may simultaneously be within the boundaries of multiple geofences.

The Field of View 116 is a boundary that defines a field for the mobile device 108. It may be implemented for example as a data structure (e.g., an array of information) including the latitude, the longitude, and the altitude of the asset and the boundaries of the Field of View (e.g., a radius).

In one example of the operation of the system of FIG. 1, location information relating to a changeable location of a mobile unit 108 is received at the server 102 via the network 106. At the server 102, an automatic determination is made as to whether an asset is closest in geographic proximity to the location of the mobile device where the asset is selected from a plurality of assets 112, 114, and 124. Based upon the selected asset, mobile interface information is automatically retrieved from the database 104 where this information is specifically associated with the selected asset 112, 114, or 124. The mobile interface information is automatically sent to the mobile unit 108 for display (e.g., via the client 110) to the user without any interaction from the user.

In other aspects, the mobile interface information is received at the mobile device 108 and presented to the user on a display of the mobile unit 108. In other aspects, the at least one of the plurality assets has defined about it a geofence and the geofence defines a boundary about the asset 112, 114, and 124. In other aspects, detection is made when the user enters the periphery of the geofence 118, 120, or 124.

In other examples of operation, a current Field of View 116 is defined for a client 110. The Field of View 116 defines a geographic area and the client 110 being operated on a mobile unit 108. Assets 112 and 114 that are disposed within the current Field of View 116 are determined. First information concerning the assets 112, 114 that are geographically located within the Field of View 116 is displayed and second information concerning asset 124 that is not geographically located within the Field of View 116 is not displayed. The first information is displayed as a mobile interface display.

In some aspects, the assets 112, 114, and 124 are associated with control devices. In some examples the Field of View is generally circular in shape while in other examples the Field of View is generally non-circular in shape.

As mentioned, the geofence region is also not required to be circular. If a user is within a geofence of an asset the automatic navigation feature may be activated. In one example, specific checks are made when a user is within multiple geofences such that a single most desirable geofence will be selected as the one with highest priority. These checks may be decisions based on the context a user is most interested. An example might include, but is not limited to alarm information for an asset where assets with higher priority alarm information would be preferred over those with lower priority. Automatic navigation can be used to move from any level in a hierarchy, or any place in an application, to transition into a detailed screen containing data related to the asset whose geofence has been entered/traversed. Automatic navigation may also be used for dynamically updating collections or summaries (to mention two examples) where a user may be within multiple geofences and a visualization may present data or graphics.

Automatic navigation is not necessarily tied to the physical location of a user, although that is one example. Automatic navigation may also be used in any situation where a context is specified with respect to any identifiable information for assets. While geospatial information is one type of identifier, other identifiers may also be used with this system allowing for intelligent application transitioning with a minimum of user input. These identifiers may include alarm severity, near-field communications, and bar-codes to mention a few examples.

Figure 2:
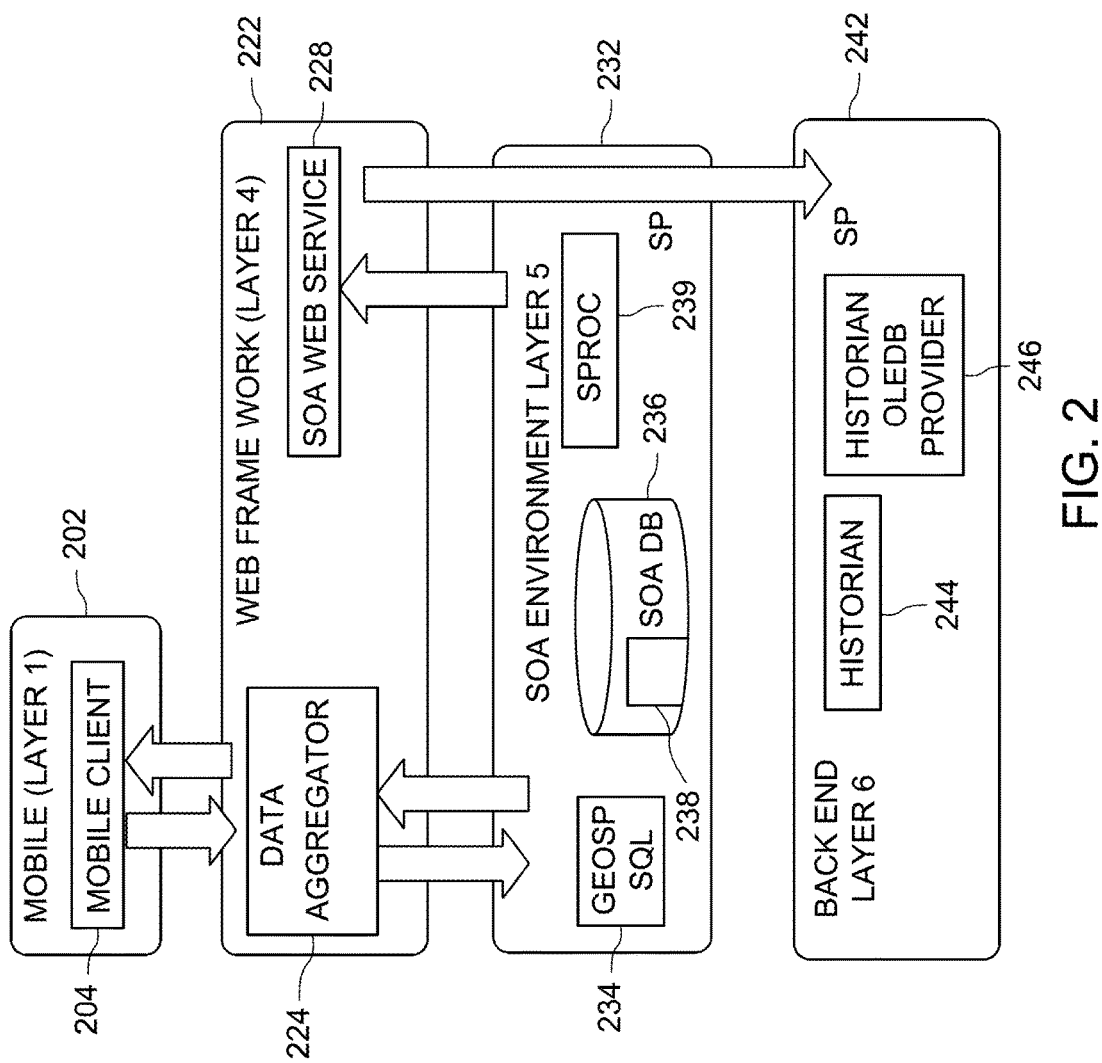
FIG. 2 comprises a block diagram of a system that provides automatic navigation and Field of View features according to various aspects of the present invention.

Referring now to FIG. 2, one example of the information flow for a system that provides automatic navigation and Field of View features is described. A mobile unit 202 includes a mobile client 204. The mobile client 204 provides various applications such as providing visualizations (e.g., mobile device interfaces such as web or other types of display pages) to users. In the current implementation, a Web frame layer 222 includes a data aggregator 224 (that receives requests from and transmits information to the mobile unit 202); and a Service oriented Architecture (SOA) web service 228 (whose purpose is to provide access to databases). These may all implemented as software functions as known to those skilled in the art.

A SOA environment layer 232 includes a GEO Table 238 inside the SQL Databases SOA database 236 and an equipment stored procedures (sproc) module 239 (that includes stored procedures that access the SQL Tables for SOA storage.). A GEIP product back end layer 242 includes a historian 244 (which has a purpose of storing historical time series data) and a Historian OLEDB Provider (which has a purpose of accessing historical data via SQL-like queries).

Figure 3:
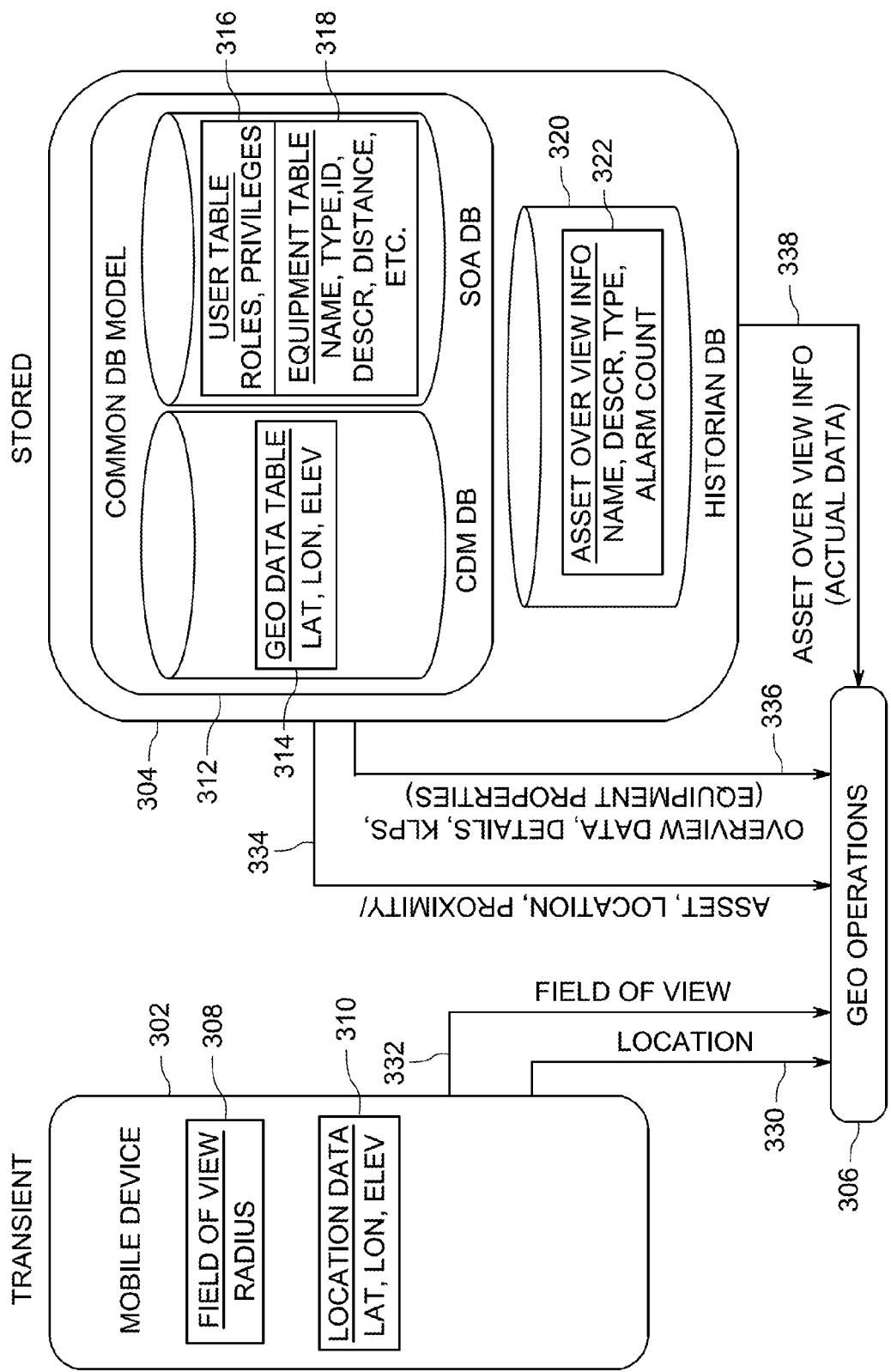
FIG. 3 comprises a block diagram of a memory structure of a system that provides automatic navigation and Field of View features according to various aspects of the present invention.

Referring now to FIG. 3, one example of a system 300 for providing automatic navigation and Field of View features is described. The system includes a mobile unit 302, a memory arrangement 304, and a geo operations server 306.

The mobile unit 302 includes and has stored in its memory a Field of View data 308 and location data 310. The memory arrangement 304 includes a common database model 312 (including a geo data table 314, a user table 316, and an equipment table 318) and a historian database 320 with an asset over view information table 322 (including names, descriptions, types, and alarm counts).

The mobile unit 302 provides location information 330 and Field of View information 332 to the geo operations server 306. The memory arrangement 304 provides asset, location and proximity information 334, equipment properties (including overview data, and details of key performance indicators (KPIs) and Alarms) 336, and asset overview information 338 (which is actual visualization data to be displayed) to the geo operations server 306.

Figure 4:
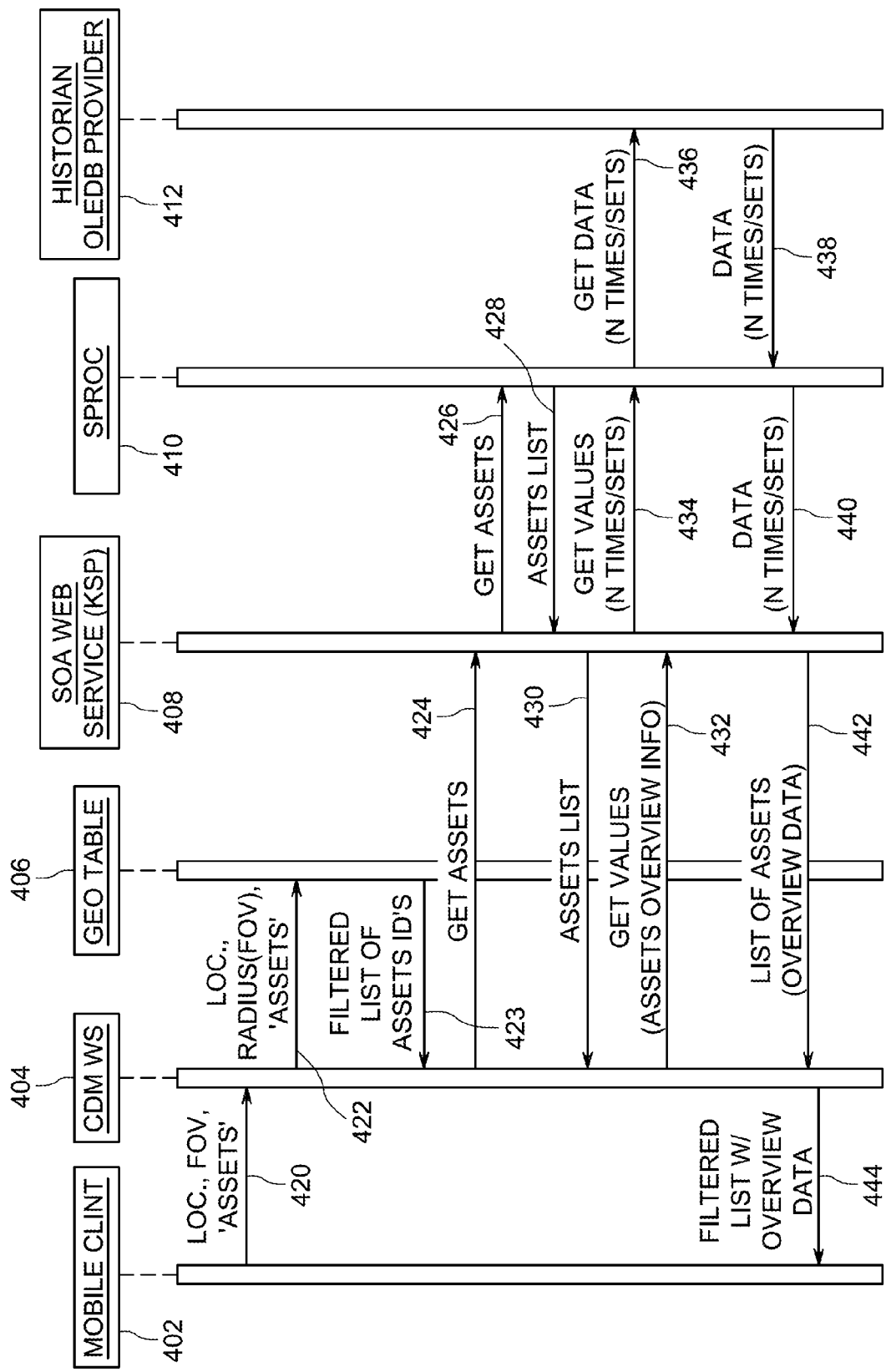
FIG. 4 comprises a flowchart of an approach for providing automatic navigation and Field of View features according to various aspects of the present invention.

As shown, the mobile client information changes while the information is stored. Referring now to FIG. 4, one example of an approach for providing automatic navigation is described. This sequence diagram shows interactions between the mobile client 402, a common data model web service (CDM WS) application 404 (that determines the nearest asset or applies some other criteria), a geo table 406, a SOA Web Service provider 408, an equipment sproc 410, and a Historian Object Linking and Embedding in Database (OLEDB) provider 412. The mobile client 402 may be a software application that runs on a mobile device (e.g., that displays information to a user). The CDM WS application 404 may be a web interface at a server. The geo table 406 may, for example, be the geo data table 314 in FIG. 3. The SOA web service provider 408 provides access to databases. The equipment sproc 410 provides access the SQL Tables for SOA storage and a Historian OLEDB provider 412 provides access to historical data via SQL-like queries. These entities are implemented as programmed software.

At step 420, the mobile client 402 begins by sending a request for Assets information to the CDM WS application 404. The request includes location information (e.g., latitude, longitude, and altitude) and Field of View information (e.g., radius). At step 422, the CDM WS application 404 sends a request to the Geo Table 406 for a filtered list of Assets ID's. The filtered list of assets includes only those assets that are within a FoV. At step 423, a filtered list of assets is returned from the Geo Table 406. At step 424, the CDM WS application 404 then sends a request to SOA WS 408 to get those Assets. At step 426, the SOA Web Service provider 408 requests the Assets List from the equipment sproc 410. At step 428, an assets list is returned to the SOA Web Service provider 408. The assets list includes name, description, type, alarm rollup, and other summary data. At step 430, the asset list is sent to the CDM WS application 404. At step 432, the CDM WS application 404 sends a get values request to the SOA Web Service provider 408. At step 434, the SOA WS provider 408 uses the Assets List to send a request to the equipment sproc 410 and then at step 436 from the equipment sproc 410 to the Historian OLEDB Provider 412 for getting values from N Sets worth of data. At steps 438 asset data is returned from the Historian OLEDB provider 412 to the sproc 410. At step 440 the asset data is sent from the sproc 410 to the SOA Web Service provider 408. At step 442, the asset data is sent from the SOA Web Service provider 408 to the CDM WS application 404. At step 442, the asset data is sent from the CDM WS 404 to the mobile client 402.

Figure 5A:
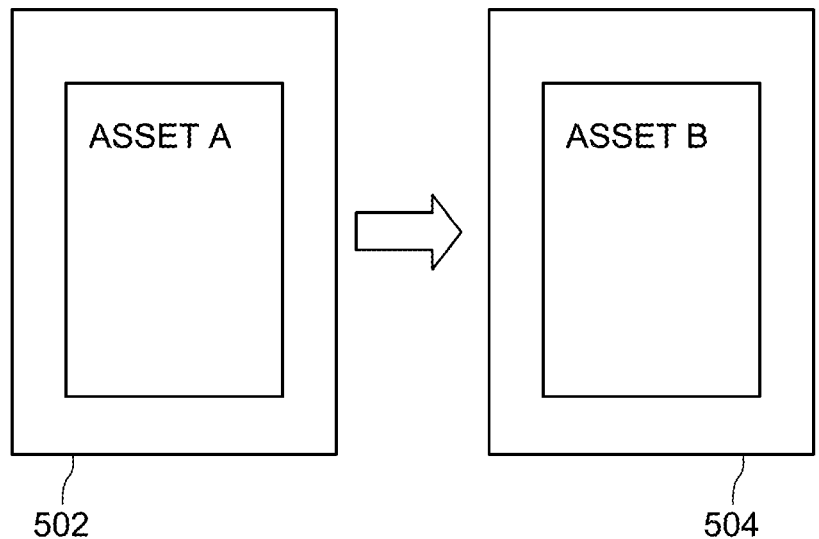
FIG. 5A comprises a screen shots showing the results of automatic navigation feature according to various aspects of the present invention.
Figure 5B:
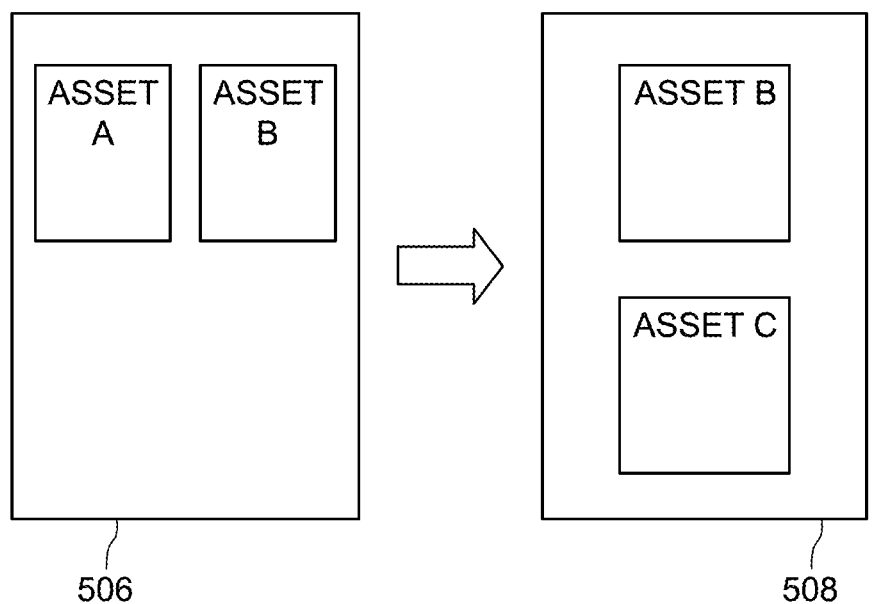
FIG. 5B comprises a screen shots showing the results of the Field of View feature according to various aspects of the present invention.

Referring now to FIGS. 5A and 5B, examples of screen shots are illustrated. These displays are presented on the display, for instance, of one of the mobile devices described herein. As shown in FIG. 5A, a first visualization 502 (e.g., a mobile device interface showing Asset A's information) changes to a second visualization 504 (a mobile device interface showing Asset B's information) as asset B becomes the closest asset. As shown in FIG. 5B, a third visualization 506 (e.g., a mobile device interface showing Asset A and Asset B information) changes to a fourth visualization 508 (a mobile device interface showing Asset B and Asset C information) as asset A moves out of the Field of View, asset B stays in the Field of View and asset C enters the Field of View. It will be appreciated that these are illustrative examples only and that other examples are possible.

Figure 6:
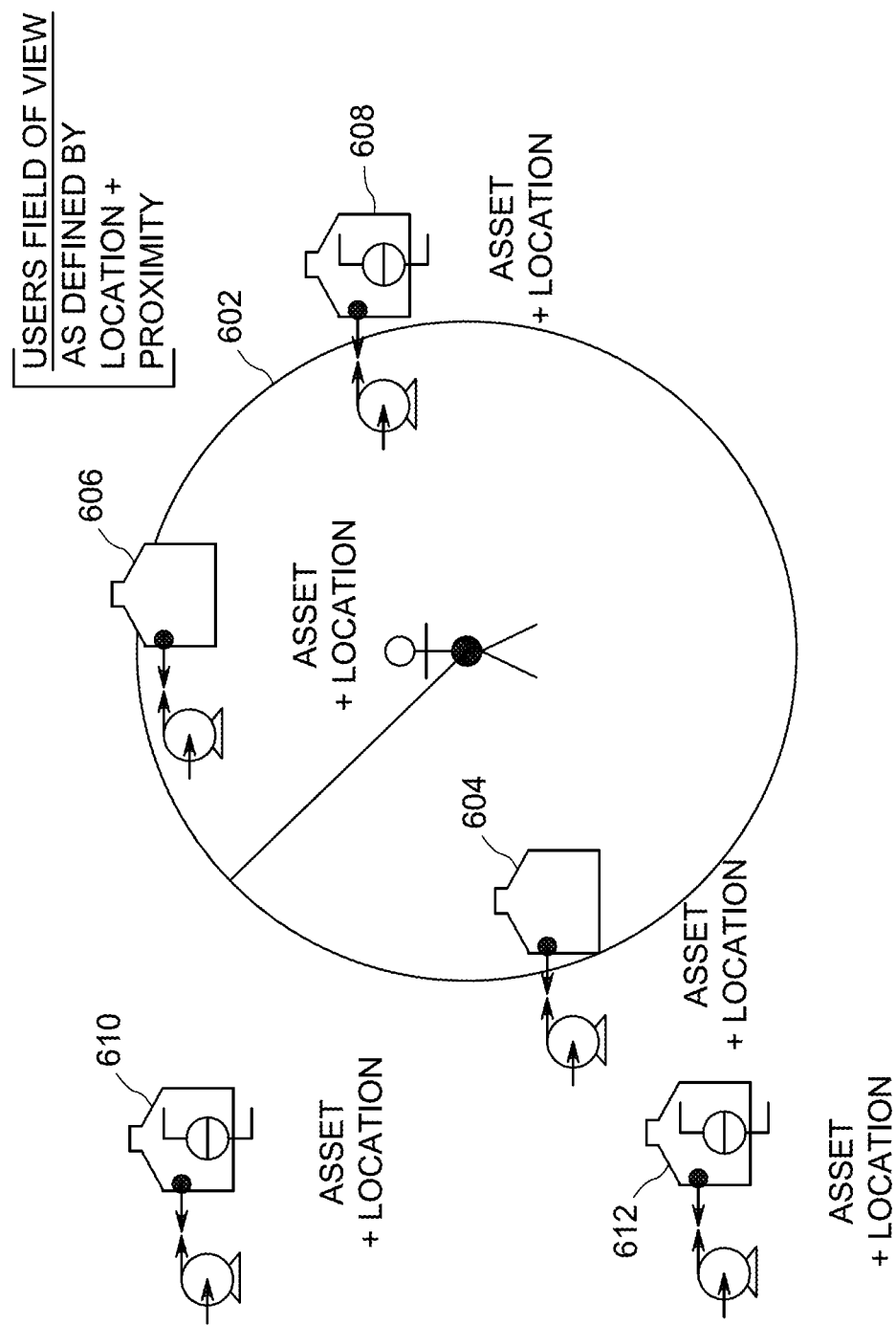
FIG. 6 comprises a diagram of a Field of View according to various aspects of the present invention.

Referring now to FIG. 6, one example of a Field of View (FoV) 602 is described. As shown, two assets 604 and 606 are within a Field of View while there are three other assets 608, 610, and 612 which are not considered within a Field of View. The Field of View 602 is defined by a circular region, but not limited as such, can be used to identify assets of interest based on geospatial proximity to a user. Those assets outside of the region defined by a Field of View are not considered for any operations. Examples of operations include list operations, data retrieval operations, plotting data on a geolocation based map visualization. Other examples are possible. In the list and data based operations, assets will either not be shown or not used in data considerations if not within a FoV 602. For the latter map-based applications, assets outside a FoV 602 will not be plotted on a map and as such, may not be interacted with via any type of user input. In other words, the FoV 602 is a filtering mechanism based on geospatial information.

Figure 7:
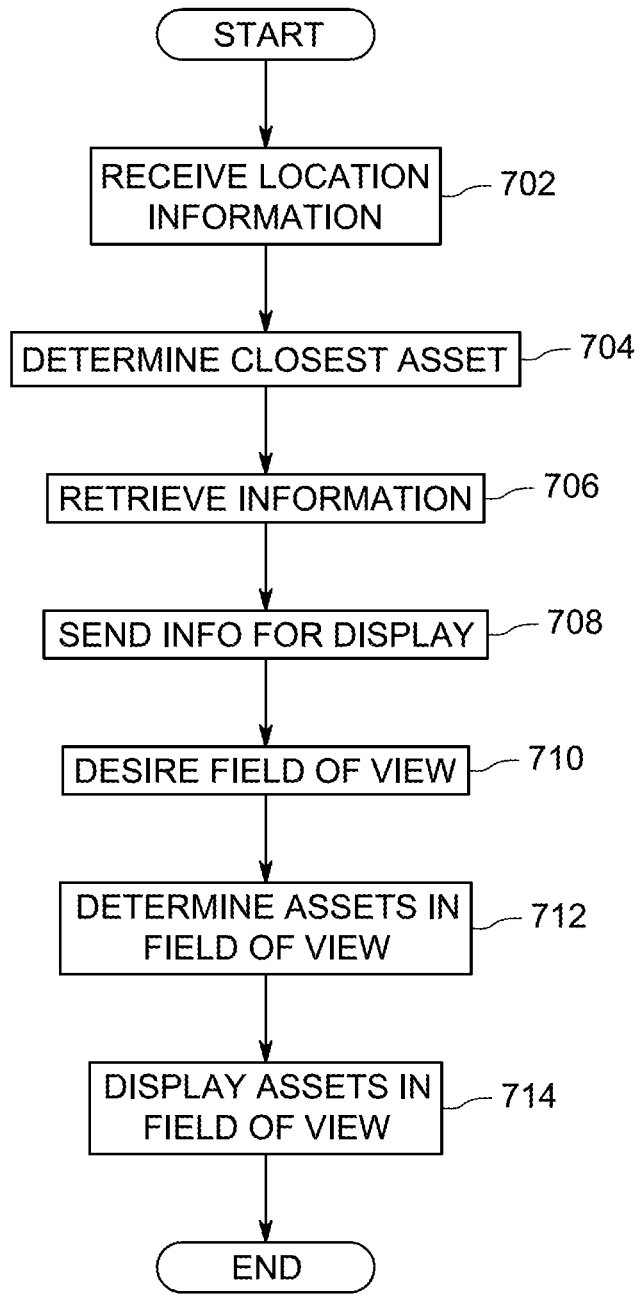
FIG. 7 comprises a flowchart of an approach for displaying information assuming Field of View is enabled according to various aspects of the present invention.

Referring now to FIG. 7, one example of an approach for providing automatic navigation and Field of View operations is described. At step 702, location information relating to a changeable location of a mobile device is received. The information may include the latitude, longitude, and altitude of a mobile device. At step 704, an automatic determination is made as to whether an asset is closest in geographic proximity to the location of the mobile device where the asset is selected from a plurality of assets. Alternatively, other criteria involving geographic nearness or not involving nearness may also be applied. At step 706, based upon the selected asset, mobile interface information is automatically retrieved where this information is specifically associated with the selected asset. At step 708, the mobile interface information is automatically sent to the mobile device for display (as a mobile device interface display) to the user without any interaction from the user.

At step 710, a current Field of View is defined for a client application. The Field of View defines a geographic area and the client application being operated on a mobile device. At step 712, assets that are disposed within the current Field of View are determined. At step 714, first information concerning the assets that are geographically located within the Field of View is displayed and second information concerning assets that are not geographically located within the Field of View is not displayed. The first information is displayed as a mobile interface display. It will be appreciated that steps 710-714 may be performed independently of or in parallel with the other steps.

Figure 8:
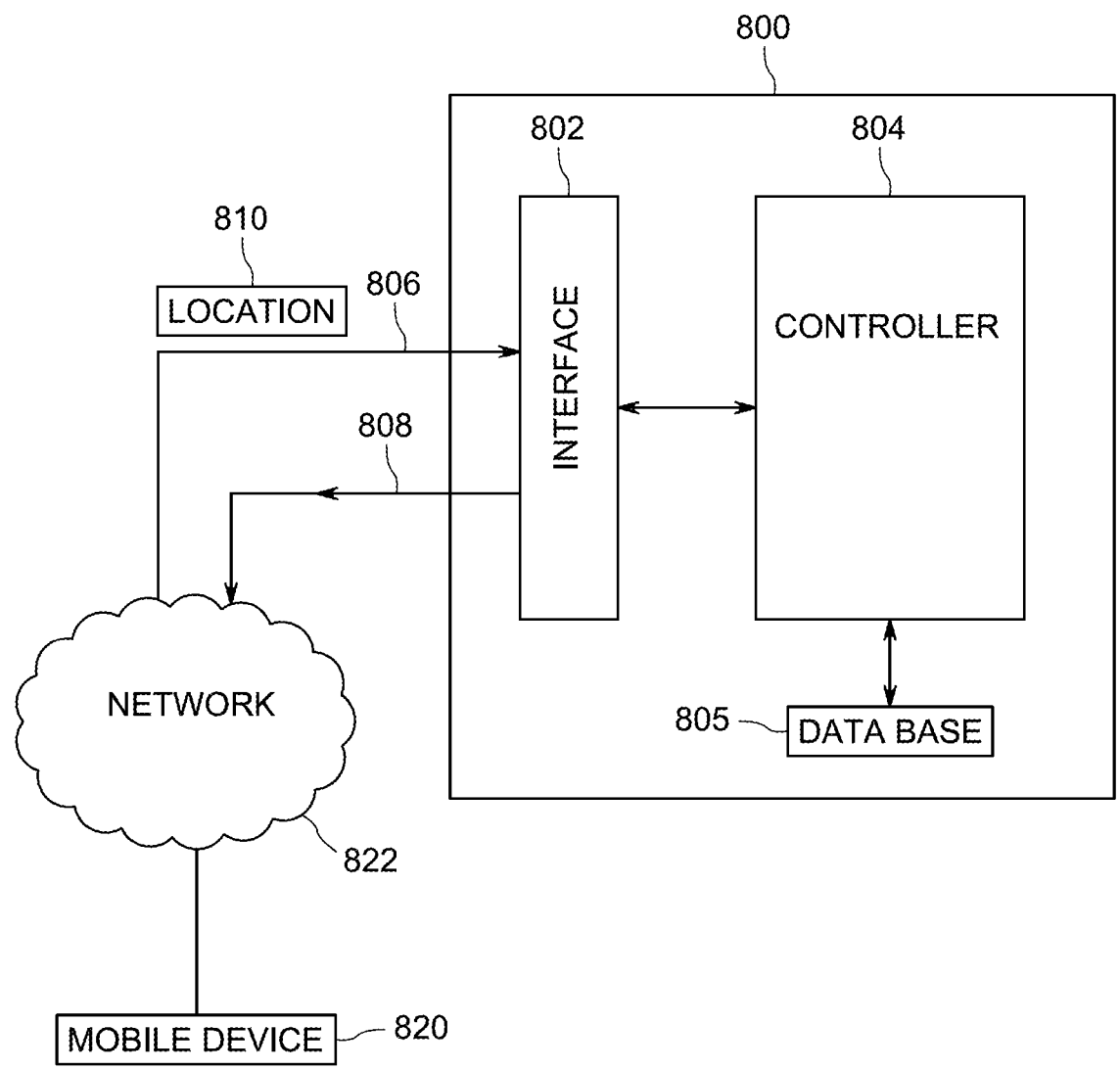
FIG. 8 comprises a block diagram of an apparatus that provides automatic navigation and Field of View features according to various aspects of the present invention.

Referring now to FIG. 8, an apparatus 800 for providing graphical information to a user includes an interface 802 and a controller 804. The interface 802 has an input 806 and an output 808, and the input 806 is configured to receive location information 810 relating to a changeable location of a mobile device 820 via a network 822. The information may include the latitude, longitude, and altitude of a mobile device. The controller 804 is coupled to the interface 802 and is configured to automatically determine an asset that is closest in geographic proximity to the location of the mobile device, the asset being selected from a plurality of assets. The interface 802 consists of all functionality needed by the controller to interface with assets and vice versa. In this respect, the interface 802 may be any combination of hardware and/or programmed software.

The controller 804 is further configured to; based upon the selected asset, automatically retrieve mobile interface information from a database 805 that is associated with the selected asset. The controller 804 is further configured to automatically send the mobile interface information to the mobile device for display to the user via the output of the interface 802 without any interaction from the user.

It will be appreciated by those skilled in the art that modifications to the foregoing embodiments may be made in various aspects. Other variations clearly would also work, and are within the scope and spirit of the invention. The present invention is set forth with particularity in the appended claims. It is deemed that the spirit and scope of that invention encompasses such modifications and alterations to the embodiments herein as would be apparent to one of ordinary skill in the art and familiar with the teachings of the present application.

What is claimed is:

1. A method of providing graphical information to a user, the method comprising:
   receiving location information relating to a changeable location of a mobile device;
   automatically determining an asset that is closest in geographic proximity to a location of the mobile device, the asset selected from a plurality of assets; wherein at least one of the plurality of assets has defined about it a geofence, the geofence defining a boundary about the asset; and detecting at least one of the plurality of assets when the user enters a periphery of the geofence;
   based upon the selected asset, automatically retrieving mobile interface information that is specifically associated with the selected asset;
   automatically sending the mobile interface information to the mobile device for display to the user without any interaction from the user; and
   defining a current Field of View for a client application, the current Field of View defining a geographic area, the client application being operated on a mobile device;
   determining assets that are disposed within the current Field of View; and
   displaying first information concerning the assets that are geographically located within the current Field of View and not displaying second information concerning assets that are not geographically located within the current Field of View, the first information being displayed as a mobile interface display.

2. The method of claim 1 further comprising receiving the mobile interface information at the mobile device and presenting the mobile interface information to the user on a display of the mobile device.

3. An apparatus for providing graphical information to a user, the apparatus comprising:
- an interface with an input and an output, the input configured to receiving location information relating to a changeable location of a mobile device;
- a controller coupled to the interface, the controller configured to automatically determine an asset that is closest in geographic proximity to the location of the mobile device, the asset selected from a plurality of assets, the controller further configured to, based upon the selected asset, automatically retrieve mobile interface information that is specifically associated with the selected asset, the controller further configured to automatically send the mobile interface information to the mobile device for display to the user via the output of the interface without any interaction from the user, wherein at least one of the plurality of assets has defined about it a geofence, the geofence defining a boundary about the asset and the controller is configured to detect at least one of the plurality of assets when the user enters a periphery of the geofence; and
- a current Field of View for a client application, the current Field of View defining a geographic area, the client application being operated on a mobile device and wherein the controller is configured to determine assets that are disposed within the current Field of View and cause the display of first information concerning the assets that are geographically located within the current Field of View and not cause to display second information concerning assets that are not geographically located within the current Field of View, the first information being displayed as a mobile interface display via the output of the interface.

4. The apparatus of claim 3 where the assets are associated with control devices.

5. The apparatus of claim 3 wherein the current Field of View is generally circular in shape.

6. The apparatus of claim 3 wherein the current Field of View is generally non-circular in shape.

* * * * *